(12) United States Patent
Sherts et al.

(10) Patent No.: US 6,533,772 B1
(45) Date of Patent: Mar. 18, 2003

(54) GUIDE WIRE TORQUE DEVICE

(75) Inventors: Charles R Sherts, Westport, CT (US); Bruce McClellan, West Lebanon, NH (US)

(73) Assignee: Innex Corporation, Fairfield, CT (US)

( * ) Notice: Subject to any disclaimer, the term of this patent is extended or adjusted under 35 U.S.C. 154(b) by 0 days.

(21) Appl. No.: 09/544,879

(22) Filed: Apr. 7, 2000

(51) Int. Cl.[7] .................. A61B 17/00; A61B 5/00; B25G 3/02; B25H 3/00
(52) U.S. Cl. .............. 606/1; 600/585; 279/42; 128/657; 81/487
(58) Field of Search ............... 606/108, 129, 606/159, 585; 128/330; 24/115, 136; 604/95; 27/28

(56) References Cited

U.S. PATENT DOCUMENTS

| | | | | |
|---|---|---|---|---|
| 3,533,439 A | * | 10/1970 | Hall | 137/595 |
| 4,463,928 A | * | 8/1984 | Ueda | 251/6 |
| 4,726,369 A | * | 2/1988 | Mar | 600/434 |
| 4,786,028 A | * | 11/1988 | Hammond | 126/380.1 |
| 4,919,389 A | * | 4/1990 | Hoekwater et al. | 251/4 |
| 4,974,811 A | * | 12/1990 | Ishida | 251/6 |
| 5,137,288 A | * | 8/1992 | Starkey et al. | 279/42 |
| 5,161,534 A | * | 11/1992 | Berthiaume | 226/127 |
| 5,259,587 A | * | 11/1993 | D'Alessio et al. | 251/297 |
| 5,312,338 A | * | 5/1994 | Nelson et al. | 600/434 |
| 5,325,746 A | * | 7/1994 | Anderson | 24/115 M |
| 5,392,778 A | * | 2/1995 | Horzewski | 600/434 |
| 5,441,497 A | * | 8/1995 | Narciso, Jr. | 606/15 |
| 5,634,475 A | * | 6/1997 | Wolvek | 600/585 |
| 5,851,189 A | * | 12/1998 | Forber | 600/433 |
| 6,033,414 A | * | 3/2000 | Tockman et al. | 606/129 |
| 6,059,484 A | * | 5/2000 | Greive | 128/912 |
| 6,129,330 A | * | 10/2000 | Guala | 251/6 |
| 6,141,896 A | * | 11/2000 | Oberst | 42/70.06 |
| 6,145,351 A | * | 11/2000 | Levenson | 292/263 |
| 6,371,571 B1 | * | 4/2002 | Tsan | 280/229 |

\* cited by examiner

*Primary Examiner*—Michael J. Milano
*Assistant Examiner*—Paul A Roberts
(74) *Attorney, Agent, or Firm*—Patrick J. Walsh (57) ABSTRACT

A guide wire torque device has an elongate tubular body with interior long axial channel and a rotary clamp wheel for gripping and ungripping a guide wire extending through the channel. The clamp wheel is accommodated within an integral enlargement of the tubular body with a segment of the wheel surface extending through the surface of the enlargement for rotation by a user's thumb in order to grip and ungrip the guide wire for feeding, withdrawing or rotating the wire with respect to a catheter.

15 Claims, 8 Drawing Sheets

GUIDE WIRE TORQUE DEVICE

BACKGROUND OF THE INVENTION

The present invention relates to catheter guide wires, and particularly to a device for feeding, holding and controlling a catheter guide wire during a medical procedure.

There are many operations or procedures made possible by using catheter-based intravascular methods which are less invasive than traditional surgery or which were not possible previously. Typical percutaneous intravascular procedures include percutaneous transluninal coronary angioplasty (PTCA), directional coronary atherectomy (DCA), angiography, angioplasty, stenting, and embolization procedures. Catheter-based methods also have demonstrated utility in other procedures including gastrointestinal and genitourinary.

In an intravascular procedure of this kind, a guide wire followed by a catheter (a small diameter, thin wall flexible tube) is inserted through a small hole made in the femoral artery in the groin area, is slowly fed through the femoral artery hole and then is slowly and tediously maneuvered through the vascular system to an operating site. In moving toward the site, the guide wire is often steered around sharp corners and through small openings. The steering is most often done by using a guide wire with a bend at the tip and by rotating the wire (torqueing) and feeding the wire forward, as it is carefully maneuvered into position.

Steering a guide wire is made more difficult because visibility of the wire within the vascular system is achieved by viewing a fluoroscope on a video screen. Visualization of the vessels and the wire often happens only for a couple of seconds at a time and appears as a two dimensional image. The person manipulating the guide wire into position must pay careful attention to the video screen and must avoid distraction by shifting attention to their hands, which are maneuvering the wire.

A new development called "Glidewire" provides a guide wire with a very slippery hydrophilic coating allowing the wire to slide through a vessel without damage. This slippery coating requires the need for a torque device to grip the wire for precise feeding and torqueing.

The constant feeding, maneuvering, positioning and repositioning of the guide wire throughout the operation requires constant gripping and ungripping of the wire in a torque device while trying to maintain the wire's position within the vascular system. This is a difficult and tedious job often requiring the retracing of the wire around tight corners or into tiny vessels after it has slipped out of position when the wire is jerked by adjusting the torque device.

In addition, positioning and repositioning of the guide wire and catheter often requires quick removal and reinsertion of the guide wire into the catheter and torque device several times during an operation. Presently, this a tedious and time consuming job. Often, the bend at the end tip of the guide wire gets hung-up as it is being feed into present torque devices, as it is fed through such torque devices, and as the wire is being fed into a catheter.

Existing guide wire torque device technology is broken down into two commonly used guide wire torque devices: a traditional collet design, and a newer one-handed slide wedge lock design.

Traditional collet design devices comprise a small tube having an outside diameter of about ¼ inch and a length of 1 to 1¼ inches. One end of the tube has four fingers formed in the tube wall which flex radially and which are covered by a larger diameter screw cap having an inner angled cam surface for moving the fingers radially. In use, the guide wire is fed through the center of the tube and end fingers. By tightening the screw cap onto the tube, the cap cams the fingers inward to clamp the wire in the same manner as a collet of a machine tool. In order to grip and ungrip the guide wire, the screw cap must be tightened and loosened. Manipulation of the wire is a three hand task: one hand must hold the wire in place while a second hand holds the collet torque device in place, and a third hand loosens and tightens the screw cap. So, two people are needed to operate an awkward device which is wasteful.

A newer one-handed device on the market is made by Cook, Inc. The Cook device is a large bulky design (3½ inches long by almost 1 inch wide) that operates the gripping mechanism by means of linear slide of a button along the axis of the device. The linear slide travels along an interior track angled relative to the axis of the guide wire. In use, the slide is pushed along the angled track gradually closing the guide wire opening and wedging the guide wire against an opposite wall thereby gripping the wire and holding it in place. This wedging action often causes doctors to complain that the device is jammed or will not release the wire. Often, doctors believe they are ungripping or releasing the wire when in fact they are actually tightening the grip on the wire. Another complaint with the linear slide lock arises from the back and forth jerking motion which often causes the guide wire tip to be shifted or dislodged inside a vessel. Another problem with this device is the difficulty in feeding a guide wire through the device without being hung-up in openings or on sharp corners. In practice, the device which is claimed to be one-handed, actually requires two hands: one to hold the wire in position and another to operate the device.

A guide wire introducer tube is now commonly used to deal with the problem of introducing the curved tip of a guide wire into a catheter tube. The introducer tube is a separate device that is used many times in a single operation. Each time it is used, the tube must be strung onto the guide wire and after starting the wire into a catheter tube, the introducer tube must be worked backward over the guide wire and removed from the trailing or opposite end of the wire.

There has been tremendous growth in the number of catheter-based operating procedures creating a need for improved instrumentation to make each aspect of such operations faster, less tedious for the physician, and safer for the patient. There is common need for accurate feeding, holding and controlling a catheter guide wire. There is need for accurate control when a catheter guide wire is being carefully maneuvered through vessels using conventional wire gripping devices that are awkward and require three hands for operation. Gripping and ungripping a guide wire using the present technology is not a smooth action and the wire tends to be dislodged from a vessel or lose position. When this happens it is a great inconvenience, wastes time, and is a danger to the patient while the physician must tediously steer the wire back into position.

Hydrophilic coatings make guide wires very slippery requiring high gripping forces to hold a wire, and also requiring sufficient mechanical advantage to rotate a wire.

SUMMARY OF THE INVENTION

The present invention provides a simple, inexpensive and disposable guide wire torque device as a solution to the difficulties encountered in practice with conventional devices. A device according to the invention securely holds and controls a catheter guide wire with one hand and with smooth operation. The device is simpler, faster to load and adjust, faster to grip and ungrip, safer for the patient, and free of jerking wire movements during catheter-based operating procedures.

A preferred embodiment of the invention comprises an elongate tubular body with interior long axial channel and a rotary clamp wheel for gripping and ungripping a guide wire extending through the channel. The clamp wheel is accommodated within an integral enlargement of the tubular body with a segment of the wheel surface extending through the surface of the enlargement for rotation by a user's thumb in order to grip and ungrip a guide wire extending through the interior channel.

The clamp wheel is mounted for rotation on an axis normal to the long axial channel. The wheel is fitted with an eccentric cam in registry with the axial channel to grip and ungrip a guide wire as the wheel rotates. The wheel has a substantially greater diameter than the eccentric cam thereby providing a substantial mechanical advantage in clamping the wire under the cam against a channel surface. The wheel further includes means such as a detent and spring for indicating to finger touch the position of the wheel thereby indicating to the user that the wire is ungripped. The wire is gripped by rotating the wheel 180° out of the detent position so that the eccentric cam clamps the wire against the interior channel.

The clamp wheel is free to rotate in either direction, that is, toward the front or rear of the gripping device. With a guide wire situated in the channel, the wheel may rotate either toward the front or rear until it grips the guide wire. To ungrip the wire, the wheel is backed off in the opposite direction.

The clamp wheel may include indicia in the form of a notch at its circumference to indicate a fully ungripped position of the wire.

In preferred form, the guide wire torque device body is symmetrical about its longitudinal axis with the body being tubular and the enlargement spherical. In addition, the spherical enlargement preferably has its center located a distance from the front of the device approximately equal to one-third the overall length of the tubular body. In this way the device can be manipulated by one hand being held with index finger on the tube ahead of the enlargement, the middle and ring fingers behind the enlargement, and the thumb atop the enlargement for engaging the clamp wheel. Accordingly, by using these four fingers, a physician may rotate the clamp wheel with the thumb to grip and ungrip the guide wire, and apply torque to the wire by rotating (or rolling) the device about its long axis. The same finger position allows the physician to feed or withdraw the wire when clamped by the device.

The clamp wheel includes a notch to act as a tactile indicator to the physician when the cam is open without requiring the user to visually check the device. A spring finger clicks into the detent on the wheel to indicate open or ungripped position. Thus the user has tactile and audible feedback eliminating the need to visually inspect the device and divert attention from the video screen.

The clamp wheel with eccentric cam acts directly on the wire for gripping and ungripping. The level of thumb force increases for rotating the wheel into gripping position, and decreases as the wire is ungripped. These changes in thumb force are immediately sensed by a physician so as to be particularly aware of wire gripped position.

So the device according to the invention provides several indicators of wire condition: increase in level of thumb force for gripped wire, and audible detent click together with tactile sensation of detent and spring position for ungripped wire.

In preferred form, the rear entry of the internal channel has a conical lead-in area for ease of feeding the wire into the device. The exterior tubular surface of the body at forward outlet is shaped to promote both ease of inserting the guide wire into a catheter opening and ease of positioning and rotating the device at a low angle of attack adjacent the catheter opening.

The substantial mechanical advantage of clamp wheel diameter to eccentric cam diameter allows for a smooth gripping and ungripping stroke with low thumb force eliminating the jerking action caused by other devices. There is also substantial mechanical advantage in torqueing the wire arising from a device diameter greater than wire diameter.

A device according to the invention utilizing an eccentric cam accommodates many wire sizes including from 0.005 to 0.050 inch diameters.

The guide wire torqueing device according to the invention solves all the problems discussed with respect to conventional devices at a similar or lower cost over such devices. The device according to the invention is about 2½ inches long and under ¾ inch wide. Its symmetrical contoured shape fits comfortably in one hand and facilitates easy manipulation and torqueing of the guide wire. There is a lead-in area at the rear of the device to eliminate the need for a special guide wire introducer. The channel running through the device has a smooth surface with no obstructions for ease of loading the wire through the device. The device has a small diameter nose for ease of feeding into a catheter without getting hung-up and without a special introducer.

The invention is directed also to several modified arrangements for guide wire torqueing devices having novel aspects and are generally described as torqueing device with collet clamp having mechanical gear driven actuation; torqueing device with collet clamp with slide or lever actuation; torqueing device with collet clamp having gear reduction linear slide; torqueing device having thumb wheel in angled track; and torqueing device having slide with angled cam surface. Each of these modified arrangements provide for gripping and ungripping a guide wire for manipulating the wire in a surgical procedure.

OBJECTS OF THE INVENTION

An object of the invention is to provide a new and improved guide wire torqueing device.

Another object of the invention is to provide a guide wire torqueing device having an ergonomic, symmetrical exterior contour for ease of manipulation and rotation with one hand.

Another object of the invention is to provide a guide wire torqueing device that takes advantage of widely used thumb motion which is intuitive to medical personnel.

Another object of the invention is to provide a guide wire torqueing device with interior channel being smooth and unobstructed, with lead-in for ease receiving wire and nose contour for ease of feeding wire into a catheter.

Another object of the invention is to provide a guide wire torqueing device with clamp wheel for gripping wire with either forward or reverse rotation of clamp wheel.

Another object of the invention is to provide a guide wire torqueing device with clamp wheel and eccentric cam providing substantial mechanical advantage for smooth operation using low forces.

Another object of the invention is to provide a guide wire torqueing device with spherical enlargement to provide high mechanical advantage that remains constant throughout 360° of device rotation.

Another object of the invention is to provide a guide wire torqueing device with clamp wheel having tactile and audible indicators of wire grip position.

Another object of the invention is to provide a guide wire torqueing device in an as small as possible size that is easy to operate and easy to spin for wire rotation.

Another object of the invention is to provide a guide wire torqueing device that accommodates a range of wire sizes.

Another object of the invention is to provide several modified arrangements for guide wire torqueing devices with specific modified mechanisms for gripping and ungripping a guide wire to enable manipulation of the wire.

Other and further objects of the invention will become apparent with an understanding of the following detailed description of the invention or upon employment of the invention in practice.

A preferred embodiment of the invention has been chosen for detailed description to enable those having ordinary skill in the art to which the invention appertains to readily understand how to construct and use the invention and is shown in the accompanying drawing in which.

DETAILED DESCRIPTION OF THE PREFERRED EMBODIMENT

Figure 1:
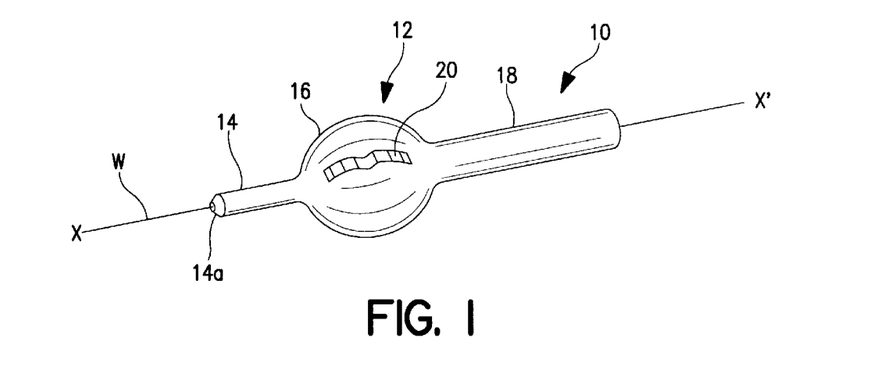
FIG. 1 is a perspective view of a preferred embodiment of guide wire torque device according to the invention.
Figure 2:
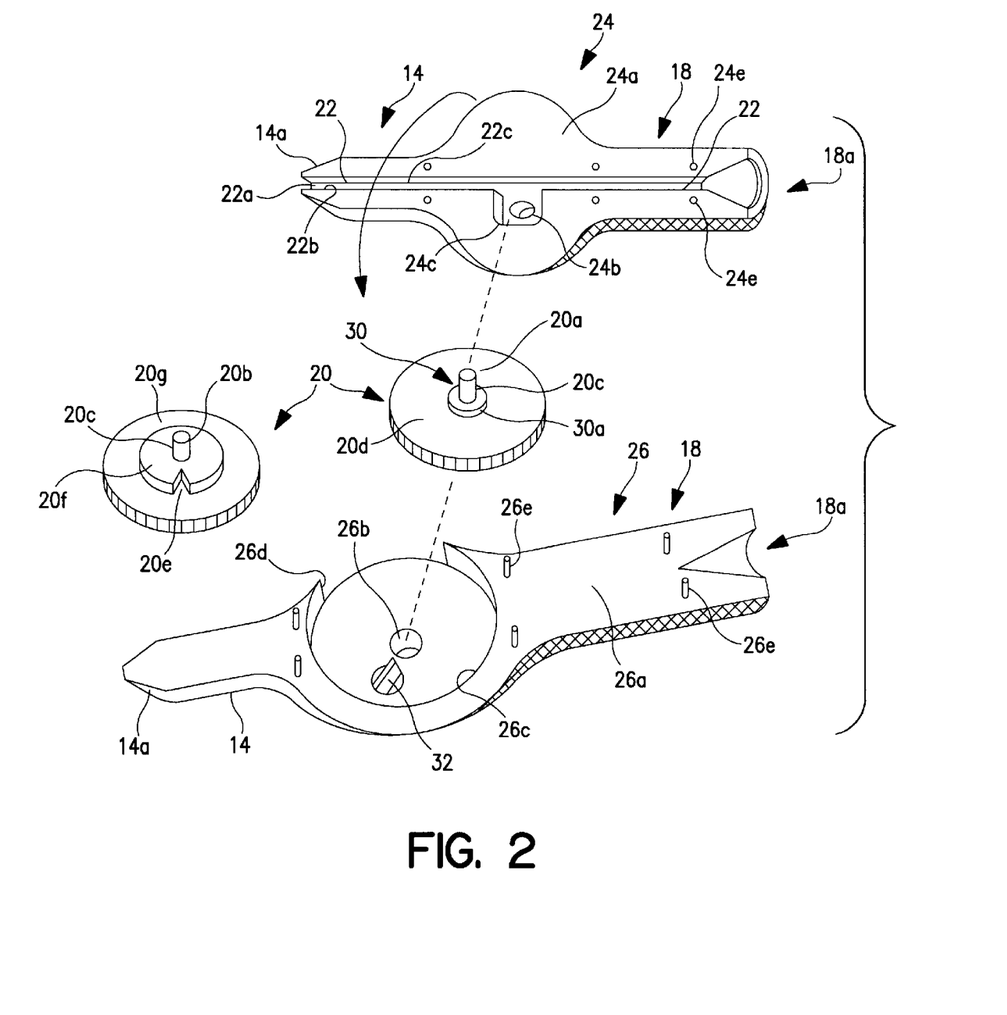
FIG. 2 is an exploded perspective view of the guide wire torque device of FIG. 1, also showing obverse and reverse faces of a clamp wheel.

Referring to the drawing, a preferred embodiment of guide wire torqueing device 10 comprises an elongate tubular body 12 with nose 14, integral spherical midsection 16, rear section 18 and clamp wheel 20 for gripping and ungripping and for torqueing a guide wire W passing axially through the device. The tubular body includes rear section 18 with conical internal entry 18a into a longitudinal channel 22 for ease of receiving a guide wire, and nose section 14 with conical tip 14a for ease of feeding the guide wire into a catheter (not shown). The nose section is shaped to promote both ease of inserting the guide wire into a catheter opening and to allow positioning and rotating the device close to the body adjacent a catheter opening. Preferably, the nose section is shorter in length and has a smaller diameter than the rear section. The torqueing device is symmetrical about its long axis x–x' represented by the guide wire.

These design aspects of the nose section and the rear section eliminate the need for a separate guide wire introducer now in common use.

Figure 5:
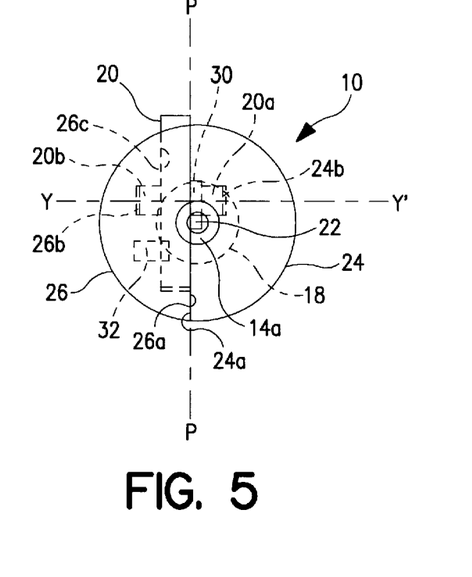
FIG. 5 is a front elevation view of an assembled torque device showing relative position of device components with respect to a longitudinal plane separating upper and lower body segments.

In a preferred embodiment, the torqueing device 10 is divided along a longitudinal plane P (FIG. 5) into upper 24 and lower 26 body segments for manufacture and assembly. The interior face 24a of the upper body segment includes the longitudinal channel 22 defining a smooth and unobstructed path for the guide wire extending from conical rear entry 18a to the tip of the nose 14. The channel is defined by base 22a and side walls 22b–c.

The interior face 24a further includes a journal bearing 24b aligned (along y–y' axis, FIG. 5) with a corresponding bearing 26b in the lower body portion for receiving the ends 20a–20b of the clamp wheel axle 20c.

Figure 6A:
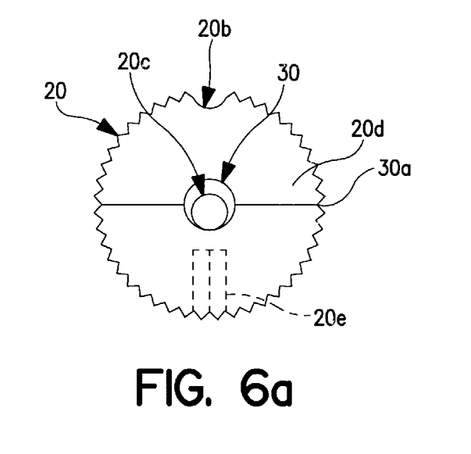
FIGS. 6a and 6b are side elevation and plan views respectively of a clamp wheel of the torque device.
Figure 6B:
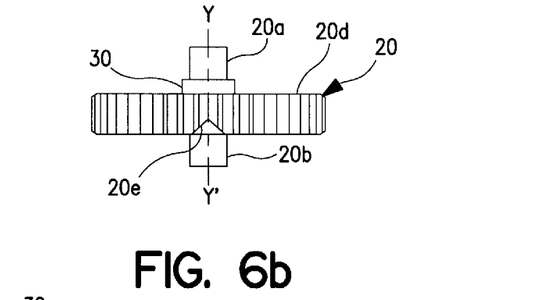
Figure 7:
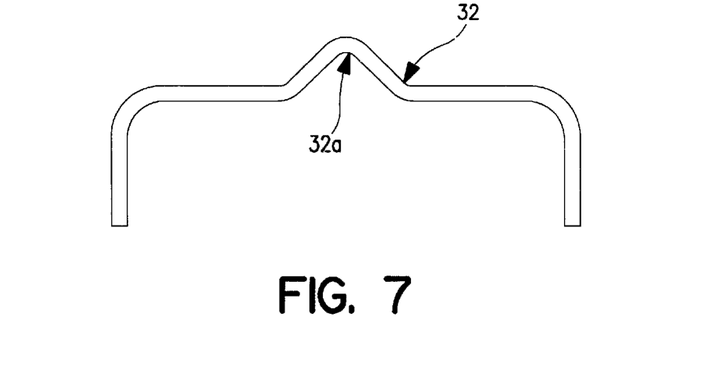
FIG. 7 is a side elevation of a detent spring.

A cam recess 24c is formed in the upper body segment around journal bearing 24b with the recess opening into the longitudinal channel 22. The cam recess accommodates rotary movement of an eccentric cam 30 fitted to the obverse face 20d of the clamp wheel as shown in FIGS. 2 and 6a.

The lower body segment 26 interior face 26a includes a generally cylindrical clamp wheel recess 26c extending through the top surface 26d of the segment to accommodate the clamp wheel for rotation about journal bearing axis y–y'. A section of the clamp wheel 20 (visible in FIGS. 1, 4a, 4b) protrudes through the spherical surface for manipulation by thumb to rotate the wheel and cam so as to grip and ungrip the guide wire.

The lower segment 26 includes conical rear entry 18a cooperating with the rear entry 18a of the upper segment to provide a converging surface for feeding the tip of the guide wire directly into the rear end of the longitudinal channel.

Matching pins 26e and holes 24e ensure proper assembly of the body segments as is well-known.

The torqueing device is fitted with rotary clamp wheel 20 for gripping and ungripping a guide wire extending through the channel. The clamp wheel is accommodated in the recess within the spherical enlargement of the tubular body with a segment of the wheel surface extending through the surface of the enlargement for rotation by a user's thumb in order to grip and ungrip a guide wire extending through the interior channel.

Figure 4A:
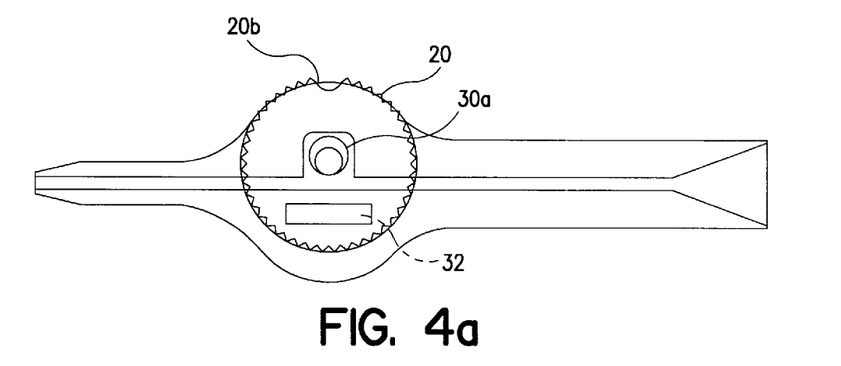
FIGS. 4a and 4b are enlarged side elevation views of the interior surfaces of upper and lower body segments of FIGS. 3a and 3b, respectively, each in subassembly with a clamp wheel shown in positions for ungripping and gripping a guide wire.
Figure 4B:
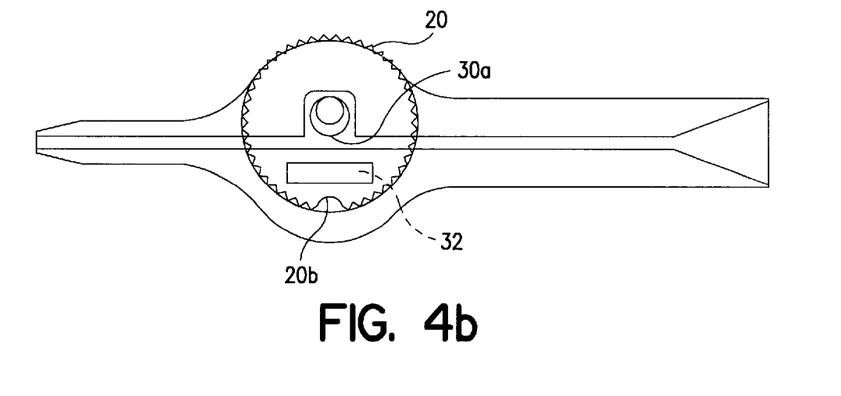

The clamp wheel rotates on y–y' axis normal to the longitudinal plane P by means of axle ends 20a–b fitted into aligned journal bearings 24b, 26b of the tubular body. The obverse face 20d of the clamp wheel is fitted with an eccentric cam 30 positioned in the cam recess with the perimeter face 30a of the cam in registry with the axial channel to grip and ungrip a guide wire as the wheel rotates. As best shown in FIGS. 4a–4b, the clamp wheel has a guide wire "ungrip" position (FIG. 4a) in which the eccentric lobe of the cam is upward in the cam recess leaving an open longitudinal channel below the recess. A guide wire is free to move through the channel past the recess and eccentric cam in this position of the wheel and cam. A 180° rotation of the clamp wheel to the position of FIG. 4b moves the eccentric cam lobe within the channel below the recess to engage and "grip" the guide wire against the channel side wall thereby preventing axial movement of the guide wire and enabling the device to torque or roll the guide wire about its long axis, and to feed or withdraw the wire with respect to a catheter.

The wheel further includes tactile and audible means for indicating to the user the position of the wheel with wire ungripped. The indicating means comprises a notch 20e in the clamp wheel for registry with a detent spring 32 mounted in the wheel recess of the lower body segment.

The cooperating detent spring and wheel notch may be as shown in FIG. 2, or as in FIGS. 4b–7.

In FIG. 2, the detent is a V-notch 20e in the perimeter of a detent disc 20f fitted to the reverse face 20g of the clamp wheel 20. The disc is concentric to the y–y' axis. A corresponding detent spring 32 located in the wheel recess registers with the notch to provide an audible and tactile click.

Figure 3A:
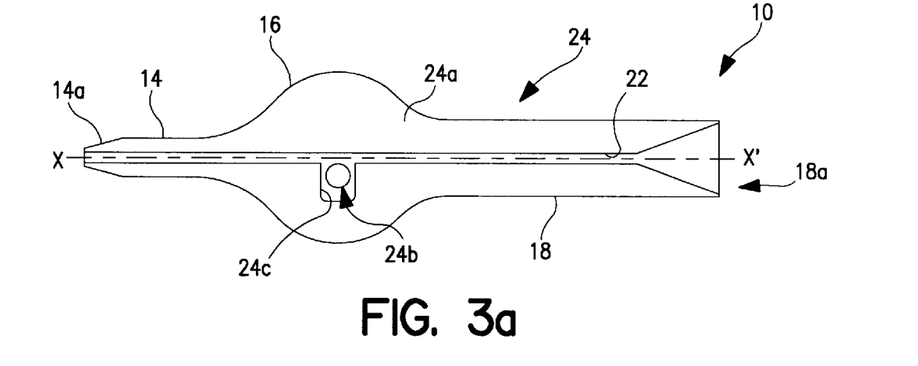
FIGS. 3a and 3b are side elevation views of the interior surfaces of upper and lower body segments, respectively, of a modified torque device according to the invention.
Figure 3B:
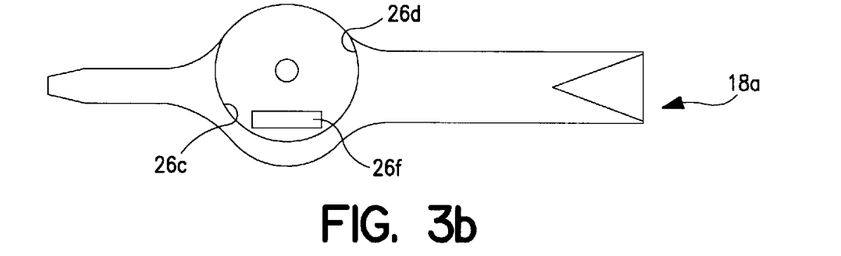

In FIGS. 4b–7, a detent spring 32 is positioned in a spring base 26f (FIG. 3b) within the wheel recess 26c. The spring has an upstanding prong 32a that registers with a notch in the reverse face of the clamp wheel to provide audible and tactile clicks.

In both FIG. 2 and in FIGS. 4b–7, the detent notch 20e and eccentric cam 30 are in opposed radial positions.

In both embodiments, as the wheel rotates, the notch engages the detent spring to give an audible "click" advising a physician that the guide wire is ungripped. The notching of the detent spring is also sensed by touch. It is observed in FIGS. 6a and 6b that the clamp wheel notch is opposed to the eccentric cam, that is, the notch is positioned on the wheel to engage the detent spring when the eccentric lobe is fully withdrawn from the longitudinal channel to ungrip the wire. In addition, a circumferential notch 20h is located on the wheel in opposed registry with the detent notch to be in a center-exposed position (FIG. 4a) under a physician's thumb. So, in use a physician has tactile and audible indicia (entry of the detent spring into the detent notch with a "click") with additional tactile indicia (the thumb notch) of the guide wire being ungripped. In addition, a physician can see the position of wheel notch 20h as in FIG. 6a, and therefore the device provides visual indicia of an ungripped wire.

The device provides additional tactile indicia to the physician through the sensing of the wheel tightening its grip on the wire. Specifically, the physician senses a greater resistance to wheel rotation as the cam tightens its grip, and a lesser resistance to wheel rotation as the cam releases the wire.

The clamp wheel has a substantially greater diameter than the eccentric cam thereby providing a substantial mechanical advantage in clamping the wire under the cam perimeter. In a preferred embodiment, the ratio of wheel to cam diameter is at least 5:1. The substantial clamp wheel mechanical advantage allows for a smooth gripping and ungripping stroke with low force and minimal or no jerking movement of the wire.

The spherical midsection in preferred embodiment has a diameter (0.68") substantially greater than the diameter of a wire in a range of wire diameters, i.e., 0.005" to 0.050", that can be used in the device. The device provides a mechanical advantage in torque of approximately 136:1 to 13.6:1 over this range of wire diameters. By reason of the spherical design of the mid-section, such mechanical advantage in torque is constantly available in any radial position of the device in a physician's hand.

It is to be noted that the clamp wheel is free to rotate on its axis toward and away from the nose allowing a physician freedom to grip the guide wire by rotating the wheel in either forward or reverse direction. The wire is ungripped by rotating the wheel opposite of the gripping direction. This design has the important advantage of gripping and ungripping with a rotation up to a maximum of 180° in either direction.

There is no likelihood of damage to the guide wire by reason of torque device components being fabricated of soft plastic parts (compared to the wire) and because of the increased tension on the thumb wheel as it rotates toward the 180° position in gripping the wire.

As noted, the guide wire torque device body is symmetrical about its longitudinal axis with the body being tubular and the enlargement spherical. In addition, the spherical enlargement preferably has its center located a distance from the front of the device approximately equal to one-third the overall length of the tubular body. In this way the device can be manipulated by one hand being held with index finger on the nose ahead of the enlargement, the middle and ring fingers on the tube behind the enlargement, and the thumb atop the enlargement. Accordingly, by using these four fingers, a physician may rotate the clamp wheel by thumb to grip and ungrip the guide wire, sense the ungripped position by touch and hearing through operation of the detent, sense the gripped position of the wire by touch, and apply torque to the gripped wire by rotating (or rolling) the device about its long axis. The same finger position allows the physician to feed or withdraw the wire when clamped by the device.

Figure 8:
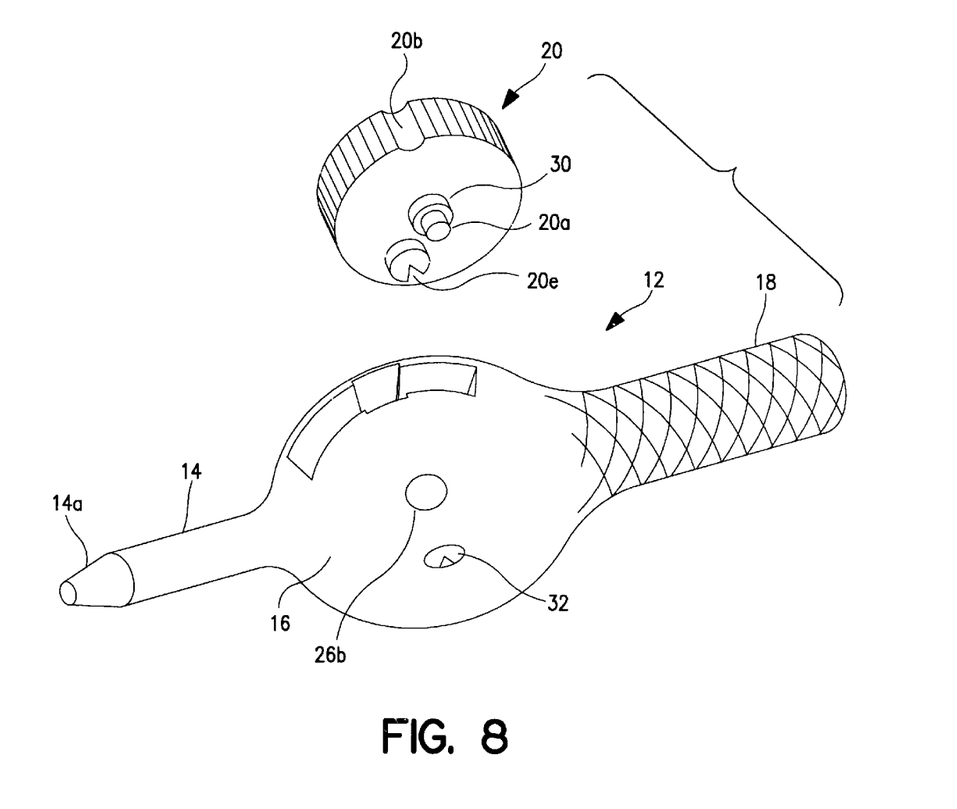
FIG. 8 is an exploded perspective view of another modified embodiment of the invention.

A modified embodiment of the invention is shown in FIG. 8 which comprises a two-piece torqueing device including main body and clamping wheel.

The main body has an exterior contour substantially the same as the embodiments of FIGS. 1–7.

In addition the interior configuration of bearing journals, clamp wheel recess, eccentric cam recess, rear conical entry, and longitudinal channel are as substantially shown and described for FIGS. 1–4b.

The clamp wheel is substantially the same in axle and eccentric cam arrangement as in FIGS. 2 and 6a. The detent disc is mounted on the same axle as the cam with the detent notch in opposed radial position from the cam. A detent spring is positioned in the main body enlargement for registry with the detent notch for audible and tactile sensing of wire position as described above.

The operation and advantages of the embodiment of FIG. 8 are substantially the same as for FIGS. 1–7.

The device may be fabricated of injection molded 10–20 percent glass filled polycarbonate with simple snap together or ultrasonic weld assembly.

Figures 9A, 9B, 9C:
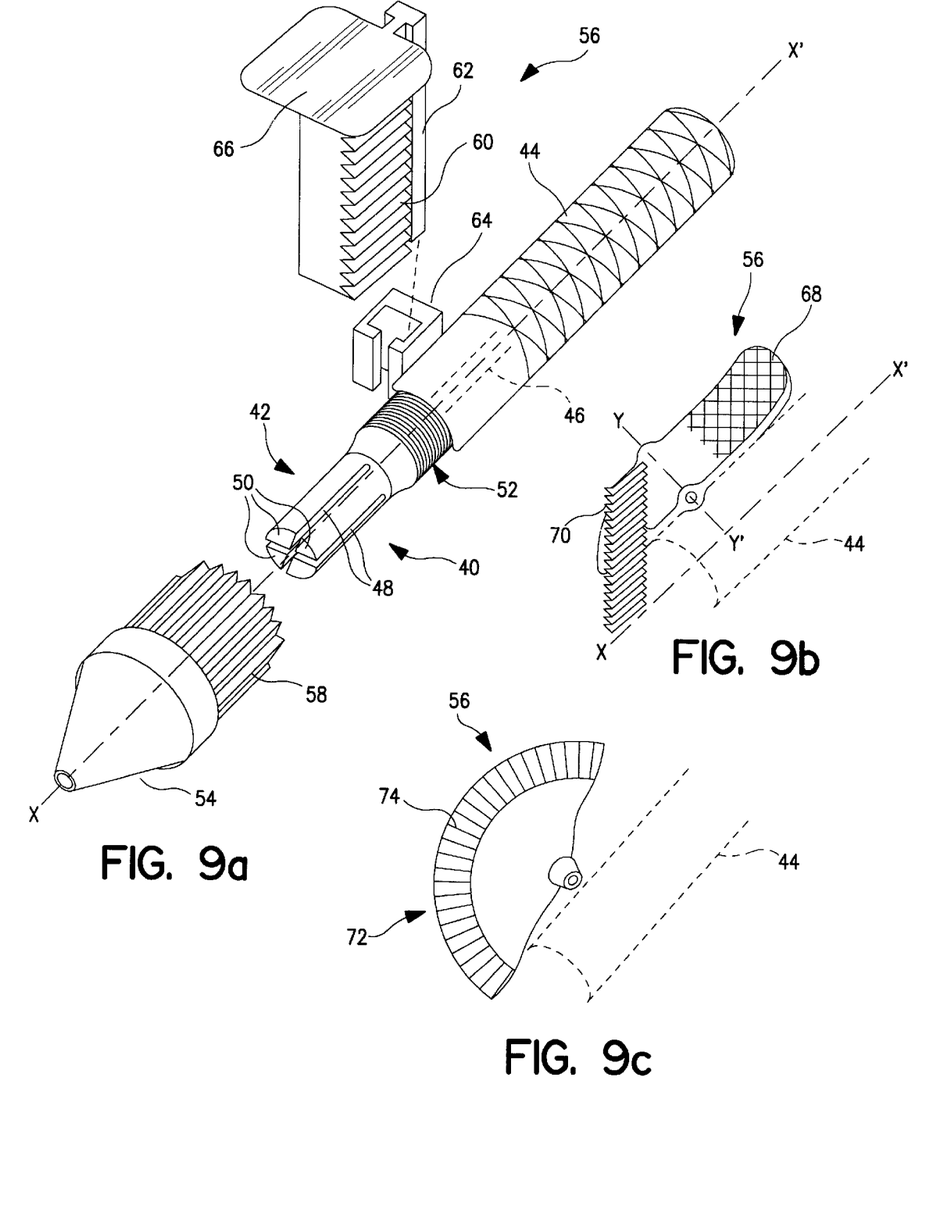
FIGS. 9a, 9b and 9c are respectively an exploded perspective view of a modified arrangement of torqueing device with collet clamp having mechanical gear driven actuation, and detail views of lever and thumb wheel gear actuators.
Figure 10:
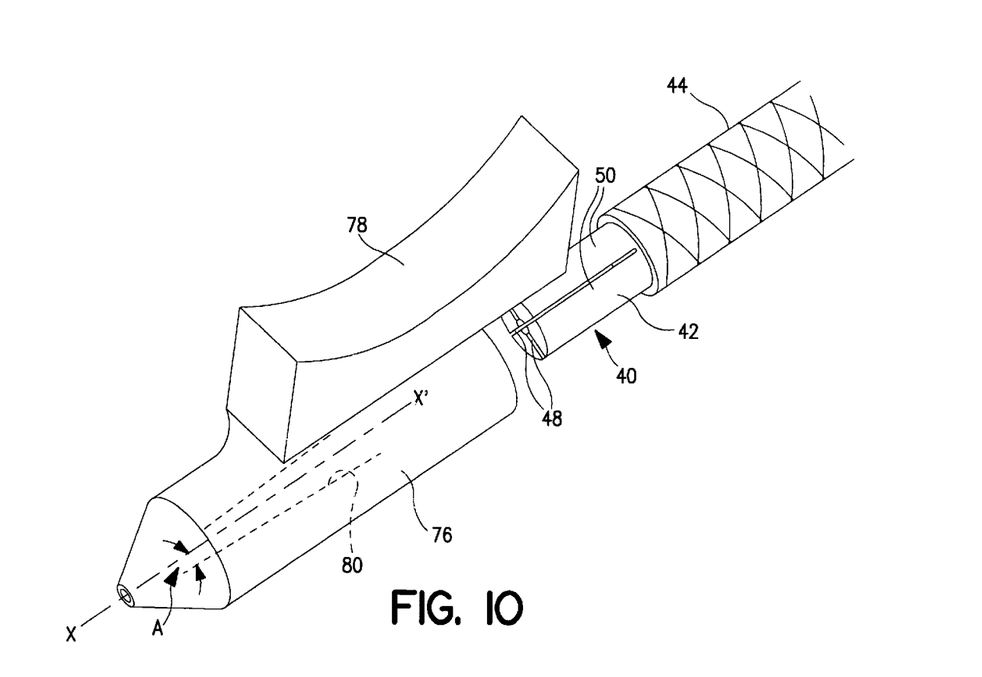
FIG. 10 is an exploded perspective view of a modified arrangement of torqueing device with collet clamp having slide actuation.
Figure 11:
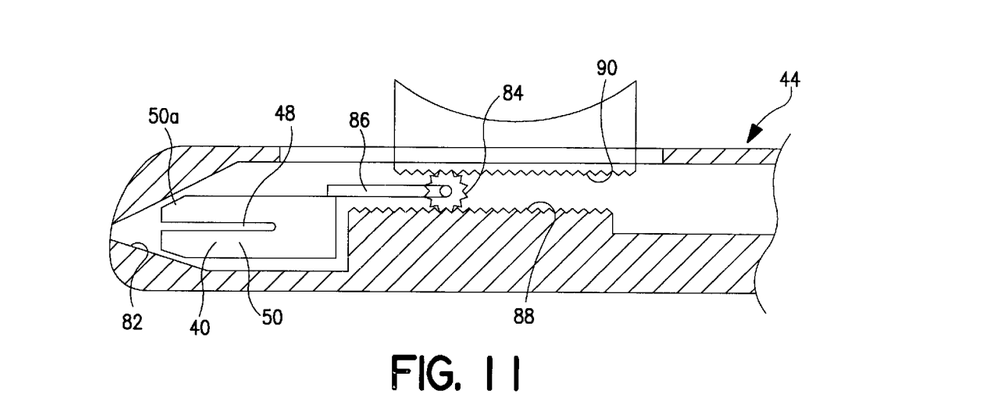
FIG. 11 is a side elevation sectional view of a modified arrangement of torqueing device with collet clamp having slide and reducing gear actuation.

FIGS. 9–11 illustrate several modified arrangements for guide wire torqueing devices having a collet clamp 40 for gripping and ungripping a guide wire. As shown in FIG. 9a, a collet clamp comprises a cylindrical end 42 integral with a torque device housing 44. The housing includes a central longitudinal passage or bore 46 along x–x' axis defining a path for a guide wire. The cylindrical end is sectioned by a plurality of grooves 48 into a plurality, preferably four, collet grip fingers 50 arranged cirumferentially about the longitudinal passage and guide wire situated in the passage.

A section 52 of the housing adjacent the collet fingers is threaded to receive a screw cap 54 for moving the collet grip fingers radially of the axial passage to grip a wire as the cap is tightened. The collet fingers have a normal spring set in which the wire is ungripped, so that by loosening the cap, the wire is ungripped.

An inventive aspect of this arrangement is the provision of a mechanical actuator 56 shown in FIGS. 9a–9c for the screw. cap to facilitate the tightening and loosening of the cap. The mechanical actuator comprises a set of gear teeth 58 along the cylindrical surface of the screw cap, and a gear rack 60 (FIG. 9a) with integral slide bar 62 positioned on the device housing by means of a slide channel 64. The gear rack has a flattened upper surface or button 66 for thumb engagement. As the button is pressed in a motion perpendicular to the longitudinal x–x' axis of the device, the gear teeth rotate the screw cap for tightening the cap which tightens the collet grip fingers for gripping the guide wire. The wire may be ungripped by loosening the screw cap.

FIGS. 9b and 9c show alternate mechanical actuators in the form of gear actuators for the screw cap gear teeth 58. One is a thumb operated lever 68 (FIG. 9b) mounted on a pivot axis y–y' normal to the long axis of the device 44. The lever has gear teeth 70 engaging and rotating the screw cap for gripping and ungripping a guide wire. By pivoting the thumb lever about the y–y' axis, its gear teeth rotate the screw cap as desired to grip and ungrip a wire.

The other mechanical actuator is a thumb wheel 72 (FIG. 9c) mounted on a pivot axis y–y' normal to the long axis of the device. The thumb wheel gear teeth 74 engage and rotate the screw cap for gripping and ungripping a guide wire.

In FIG. 10, the collet clamp grip fingers 50 of the torqueing device 44 are actuated in gripping and ungripping a guide wire by means of a sliding collet cap 76 or linear slide clamp tube fitted with a slide button 78. The clamping surface 80 on the inside of the collet cap forms a very low angle A (typically 1°–2°, measured. with respect to the longitudinal axis). The clamping surface 80 fits over the flexible collet fingers 50. As the clamp tube is moved in linear fashion by a slide button 78 against the collet fingers, the tube presses the fingers inward to clamp a guide wire situated along the axial passage of the device.

FIG. 11 illustrates an alternative guide wire torqueing device having a collet clamp 40 with grip fingers 50 for gripping and ungripping a guide wire fitted within the device housing. A conical interior surface 82 of the housing engages the frusto-conical exterior tip 50a of the grip fingers for closing the fingers in gripping a wire as the collet moves axially toward and engages the conical interior surface. The collet clamp is driven linearly by means of a reducing gear 84 affixed to the collet by a mounting flange 86 with the gear in engagement with a stationary gear track 88 on the housing and with gear teeth 90 on a linear slide button. By linear translation of the slide button, the reducing gear advances the conical tip of the collet fingers into closing engagement with the housing cone thereby closing the fingers and gripping a wire. The reducing gear provides mechanical advantage in moving the collet fingers to clamp a guide wire passing through the collet.

Figure 12A:
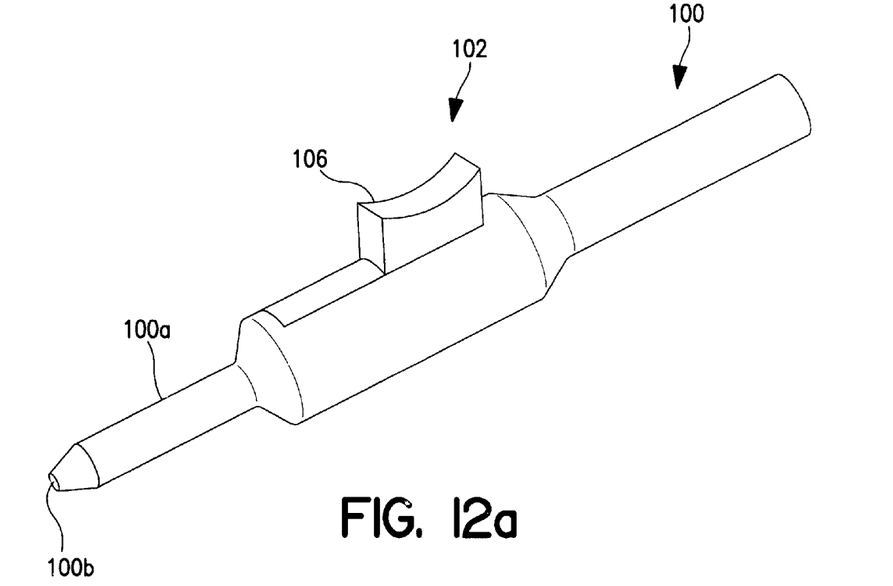
FIGS. 12a, 12b and 12c are respectively an exploded perspective view of a modified arrangement of torqueing device with collet clamp having slide with angled cam surface, and sequential side elevation sectional views thereof.
Figure 12B:
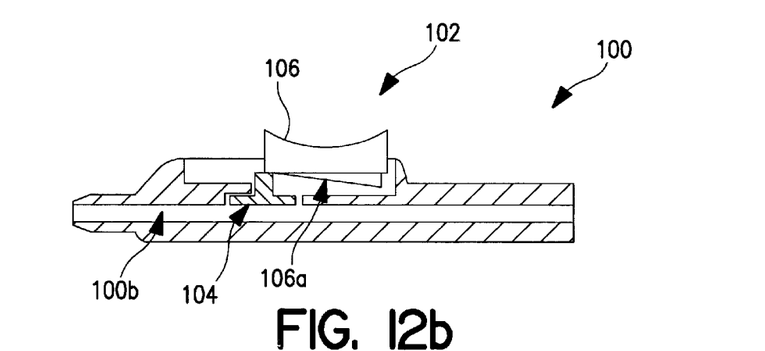
Figure 12C:
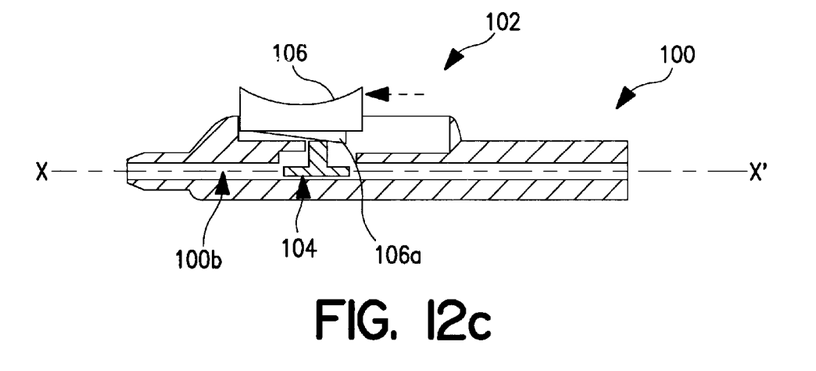
Figure 13A:
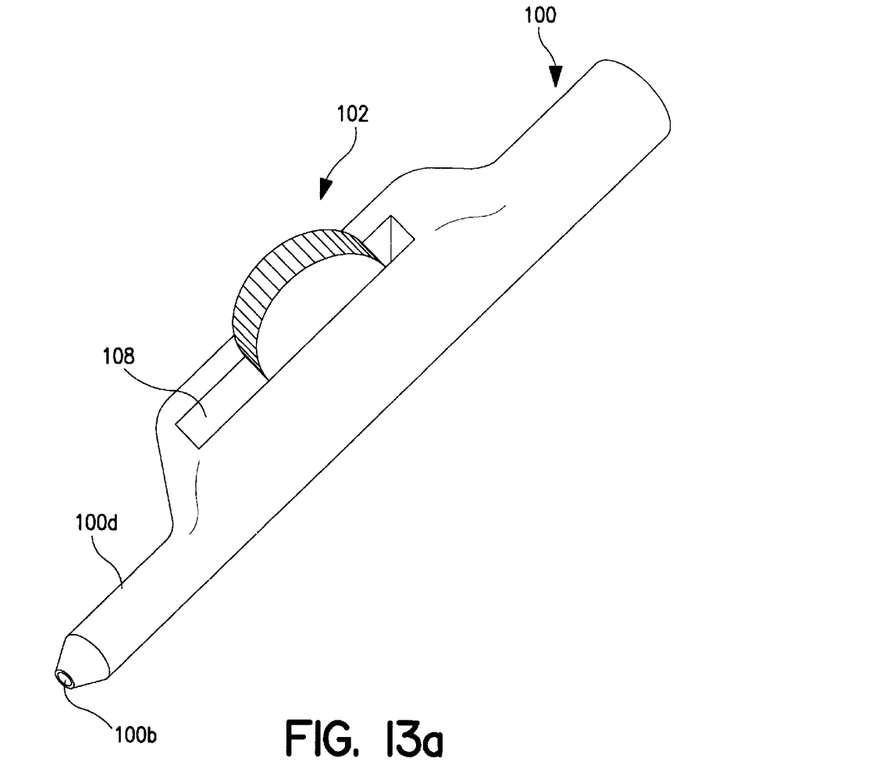
FIGS. 13a and 13b are respectively an exploded perspective view of a modified arrangement of torqueing device with actuating thumb wheel in angled track, and side elevation sectional view thereof.
Figure 13B:
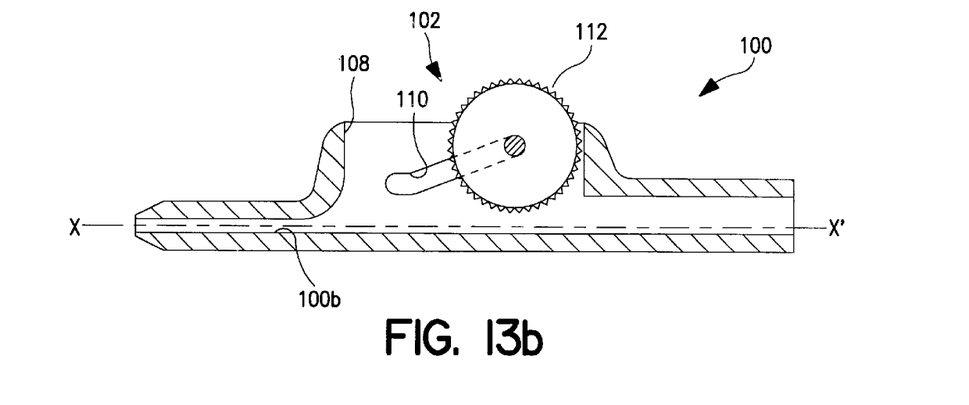

FIGS. 12–13 illustrate modified arrangements for guide wire torqueing devices 100 having a housing mounted clamp 102 for gripping and ungripping a guide wire. As shown, the housing includes a generally tubular body 100a with central longitudinal passage or bore defining a path for a guide wire.

In FIGS. 12a–12c, a section of the housing adjacent the guide wire passage receives a clamp pad 104 and a slide button 106 with angled cam surface 106a. The clamp pad moves perpendicular to the passage axis x–x' to grip and ungrip a wire. The slide button is fitted over the pad and depresses the pad to grip a wire with forward linear movement of the button. This device has the advantage of operation similar to well-known flow control valves generally used by medical personnel.

In FIGS. 13a–13b, a recess 108 in of the housing adjacent the guide wire passage has an angled track 110 which mounts a thumb wheel clamp 112 and operates on the same principle as commonly used tube roller clamps in operating rooms. As the thumb wheel rotates down the track it rolls along the angled slot and closes the space between the wheel and the wire passage to grip and ungrip a wire situated in the passage.

Various changes may be made to the structure embodying the principles of the invention. The foregoing embodiments are set forth in an illustrative and not in a limiting sense. The scope of the invention is defined by the claims appended hereto.

We claim:

1. A guide wire torqueing device comprising an elongate body having a longitudinal channel for receiving and manipulating a guide wire, the body having a nose, an enlarged mid-section, and a rear end each defining a portion of the longitudinal channel, the nose being shaped to feed a guide wire into a catheter opening, clamping means mounted in the mid-section enlargement for gripping and ungripping a guide wire extending through the channel, and the clamping means extending through the surface of the enlargement for actuation by a user's thumb for gripping and ungripping the wire whereby when the wire is gripped the user may feed, retract or apply torque to the wire.

2. A guide wire torqueing device comprising an elongate body having a longitudinal channel for receiving and manipulating a guide wire, the body having a nose, an enlarged mid-section, and a rear end each defining a portion of the longitudinal channel, the nose being shaped to feed a guide wire into a catheter opening, clamping means mounted in the mid-section enlargement for gripping and ungripping a guide wire extending through the channel, the clamping means extending through the surface of the enlargement for actuation by a user's thumb for gripping and ungripping the wire, and the rear section having an enlarged entry into the rear end of the channel for ease of feeding a guide wire into the channel.

3. A guide wire torqueing device comprising an elongate body having a longitudinal channel for receiving and manipulating a guide wire, the body having a tubular nose, an enlarged spherical mid-section, and a tubular rear end all aligned along a longitudinal axis and together defining a longitudinal channel, the nose having a conical tip to feed a guide wire into a catheter opening, clamping means mounted in the mid-section enlargement for gripping and ungripping a guide wire extending through the channel, and the nose, the midsection and the rear end defining an exterior surface of the device which is symmetrical with respect to the longitudinal axis of the device.

4. A guide wire torqueing device comprising an elongate body having a longitudinal channel for receiving and manipulating a guide wire, the body having a nose, an enlarged mid-section, and a rear end each defining a portion of the longitudinal channel, a clamping wheel mounted for rotation in the mid-section enlargement for gripping and ungripping a guide wire extending through the channel, and a section of the perimeter of the clamping wheel extending through the surface of the enlargement for actuation by a user's thumb for gripping and ungripping the wire, the clamping wheel having an eccentric cam for gripping and ungripping the guide wire as the wheel is rotated, whereby when the wire is gripped the user may feed, retract or apply torque to the wire.

5. A guide wire torqueing device comprising an elongate body having a longitudinal channel for receiving and manipulating a guide wire, the body having integral nose, enlarged mid-section, and rear end, a longitudinal channel through the body, a clamping wheel mounted for rotation in the body for gripping and ungripping a guide wire extending through the channel, the clamping wheel having an eccentric cam rotatable into and out of the channel for respectively gripping and ungripping a guide wire extending through the channel, means for rotation of the clamping wheel, the device having sensing means for indicating gripped and ungripped positions of the guide wire.

6. A guide wire torqueing device comprising an elongate body having a longitudinal channel for receiving and manipulating a guide wire, the body having a nose, an enlarged mid-section, and a rear end each defining a portion of the longitudinal channel, a clamping wheel mounted for rotation in the mid-section enlargement, the clamping wheel having an eccentric cam rotatable into and out of the channel for respectively gripping and ungripping a guide wire extending through the channel, the eccentric cam being adapted to grip and ungrip a wire in a 180° rotation of the wheel in either forward or reverse direction, and a section of the perimeter of the clamping wheel extending through the surface of the enlargement for actuation by a user's thumb for gripping and ungripping the wire.

7. A guide wire torqueing device comprising an elongate body having a longitudinal channel for receiving and manipulating a guide wire, the body having integral nose, enlarged mid-section, and rear end, a longitudinal channel through the body, a clamping wheel mounted for rotation in the body for gripping and ungripping a guide wire extending through the channel, the clamping wheel having an eccentric cam rotatable into and out of the channel for respectively gripping and ungripping a guide wire extending through the channel, the body having a detent spring mounted therein, the clamping wheel having a notch for registry with the detent spring to indicate by audible and tactile sensation a position of the wheel with respect to the guide wire.

8. A guide wire torqueing device as defined in claim 7 in which the notch and spring detent cooperate to indicate ungripped position of the wheel with respect to the guide wire.

9. A guide wire torqueing device as defined in claim 7 in which the diameter of the wheel is greater that the diameter of the cam to provide mechanical advantage in gripping the wire.

10. A guide wire torqueing device as defined in claim 7 in which the mechanical advantage is at least 5:1.

11. A guide wire torqueing device as defined in claim 7 in which the gripping of the wire by the cam provides tactile sensation indicating to the user gripped position of the wire.

12. A guide wire torqueing device as defined in claim 7 wherein the wheel is rotatable in forward and reverse direction to grip and ungrip a wire.

13. A guide wire torqueing device as defined in claim 7 in which the channel accommodates wires in a diameter range of 0.005 to 0.050 inches.

14. A guide wire torqueing device as defined in claim 13 in which the mid-section diameter is 0.68 inches to give a mechanical advantage of 136:1 to 13.6:1 over the range of wire diameters accommodated.

15. A guide wire torqueing device as defined in claim 6 which is gripped in one hand with index finger under the nose, middle and ring finger under the rear section, and the thumb atop the mid section for manipulating the clamp wheel.

* * * * *